US009006293B2

(12) United States Patent
Yamaguchi et al.

(10) Patent No.: US 9,006,293 B2
(45) Date of Patent: Apr. 14, 2015

(54) COMPOSITIONS CONTAINING XANTHOHUMOL-CYCLODEXTRIN COMPLEXES (75) Inventors: Naoto Yamaguchi, Bethesda, MD (US); Mitsunori Ono, Lexington, MA (US)

(73) Assignee: Flaxan GmbH & Co. KG, Nuremberg (DE)

( * ) Notice: Subject to any disclaimer, the term of this patent is extended or adjusted under 35 U.S.C. 154(b) by 706 days.

(21) Appl. No.: 12/919,192

(22) PCT Filed: Feb. 26, 2009

(86) PCT No.: PCT/US2009/001301
§ 371 (c)(1),
(2), (4) Date: Dec. 29, 2010

(87) PCT Pub. No.: WO2009/108379
PCT Pub. Date: Sep. 3, 2009

(65) Prior Publication Data
US 2011/0086815 A1    Apr. 14, 2011

Related U.S. Application Data (60) Provisional application No. 61/031,762, filed on Feb. 27, 2008.

(51) Int. Cl.
*A61K 31/045* (2006.01)
*A01N 31/14* (2006.01)
*A61K 31/075* (2006.01)
*A01N 43/04* (2006.01)
*A61K 31/715* (2006.01)
*A23L 1/30* (2006.01)
*C08B 37/16* (2006.01)
*C08L 5/16* (2006.01)

(52) U.S. Cl.
CPC ........... *A23L 1/3002* (2013.01); *C08B 37/0015* (2013.01); *C08L 5/16* (2013.01); *A23V 2002/00* (2013.01)

(58) Field of Classification Search
CPC ........... C07C 49/255; A61K 47/48969; A23L 1/3002; C08L 5/16; C08B 37/0015; A23V 2200/3262; A23V 2002/00; A23V 2250/2116; A23V 2250/5112
USPC ................................... 514/58, 715, 718, 730
See application file for complete search history.

(56) References Cited

U.S. PATENT DOCUMENTS

| 4,490,405 | A | 12/1984 | von Horst et al. |
| 5,011,594 | A | 4/1991 | Haeffner et al. |
| 5,866,162 | A | 2/1999 | Grattan |
| 6,867,332 | B1 | 3/2005 | Biendl et al. |
| 2004/0121040 | A1* | 6/2004 | Forster et al. ............ 426/15 |
| 2004/0219238 | A1 | 11/2004 | Nishiyama et al. |
| 2007/0042063 | A1 | 2/2007 | Tripp et al. |
| 2007/0155695 | A1 | 7/2007 | Wirth et al. |
| 2007/0218155 | A1 | 9/2007 | Kuhrts |
| 2011/0207697 | A1* | 8/2011 | Ono et al. .................. 514/58 |

FOREIGN PATENT DOCUMENTS

| JP | 2007289185 A | 11/2007 | |
| WO | WO-2003006037 A1 | 1/2003 | |
| WO | WO 2005/068484 A1 * | 7/2005 | ............ C07H 17/07 |
| WO | WO-2006066941 A2 | 6/2006 | |
| WO | WO-2007016578 A2 | 2/2007 | |

OTHER PUBLICATIONS

Stevens, J.F., Page, J.E. (2004) Xanthohumol and related prenylflavonoids from hops and beer: to your good health! Phytochemistry, vol. 65, p. 1317-1330.*
Thompson, D. Chaubal, M.V. (2002) Cyclodextrins (CDS)— Excipients by Definition, Drug Delivery Systems by Function (Part I: Injectable Applications). Drug Delivery Technology, vol. 2, No. 7, p. 34, 36 and 38.*
C.L. Miranda et al., Antiproliferative and Cytotoxic Effects of Prenylated Flavonoids from Hops (*Humulus lupulus*) in Human Cancer Cell Lines, Food and Chemical Toxicology, vol. 37, pp. 271-85 (1999).
N. Tabata et al., "Xanthomumols, Diacylglycerol Acyltransferase Inhibitors, From *Humulus lupulus*", Phytochemistry, 46(4), pp. 683-687, (1997).
J.F. Stevens et al., "Inhibition of Peroxynitrite-Mediated LDL Oxidation by Prenylated Flavonoids: The a,b-Unsaturated Keto Functionality of 2'-Hydroxychalcones as a Novel Antioxidant Pharmacophore", Chem. Res. Toxicol., 16(10), pp. 1277-1286 (2003).
H. Nozawa et al., "Xanthohumol, the chalcone from beer hops (*Humulus lupulus* L), is the ligand for farnesoid X receptor and ameliorates lipid and glucose metabolism in KK-Ay mice", Biochemical and Biophysical Research Communications, 336(3), pp. 754-761 (2005).
Albini et al., "Mechanisms of the antiangiogenic activity by the hop flavonoid xanthohumol: NF-kB and Akt as targets", The FASEB Journal, vol. 20, pp. 527-529 (2005).
V.E. Buckwold et al., "Antiviral activity of hop constituents against a series of DNA and RNA viruses", Antiviral Research, 61(1), pp. 57-62 (2004).
Q. Wang et al., "Xanthohumol, a novel anti-HIV-1 agent purified from Hops *Humulus lupulus*", Antiviral Research, vol. 64, pp. 189-194 (2004).
J. Alexander et al., "(Acyloxy)alkyl Carbamates as Novel Bioreversible Prodrugs for Amines: Increased Permeation through Biological Membranes", Journal of Medicinal Chemistry, vol. 31, pp. 318-322 (1988).

(Continued)

*Primary Examiner* — Scarlett Goon
(74) *Attorney, Agent, or Firm* — Locke Lord LLP; Jeffrey D. Hsi (57) ABSTRACT

The invention provides compositions comprising xanthohumol/cyclodextrin complexes that are water soluble and that have increased stability relative to xanthohumol alone.

24 Claims, 3 Drawing Sheets

(56) References Cited

OTHER PUBLICATIONS

A.J. Verbiscar et al., "Carbamate Ester Latentiation of Physiologically Active Amines", Journal of Medicinal Chemistry, 13(60, pp. 1176-1179 (1970).

V.J. Stella et al., "Prodrugs and Site-Specific Drug Delivery", Journal of Medicinal Chemistry, 23(12), pp. 1275-1282 (1980).

S. Kodama et al., "Enantioseparation of Isoxanthohumol in Beer by Hydroxpropyl-g-cyclodextrin-Modified Micellar Electrokinetic Chromatography", J. Agric. Food Chem., vol. 55, pp. 6547-6552 (2007).

R. Ficarra et al., "Study of flavonoids/b-cyclodextrins inclusion complexes by NMR, FT-IR, DSC, X-ray invetigation", vol. 29, pp. 1005-1014 (2002).

M.L. Calabro et al., "Effects of a- and b-cyclodextrin complexation on the physico-chemical properties and antioxidant activity of some 3-hydroxyflavones", Journal of Pharmaceutical and Biomedical Analysis, vol. 35, pp. 365-377 (2004).

S. Tommasini et al., "Improvement in solubility and dissolution rate of flavonoids by complexation with b-cyclodextrin", Journal of Pharmaceutical and Biomedical Analysis, vol. 35, pp. 379-387 (2004).

C. Lucas-Abellan et al., "Encapsulation of Quercetin and Myricetin in Cyclodextrins at Acidic pH", Journal of Agricultural and Food Chemistry, vol. 56, pp. 255-259 (2008).

M.C. Bergonzi et al., "Studies on the interactions between some flavonols and cyclodextrins", Bioorganic & Medicinal Chemistry Letters, vol. 17, pp. 5744-5748 (2007).

S.H. Lee et al., "Enhanced Bioavailability of Soy Isoflavones by Complexation with b-Cyclodextrin in Rats", Biosci. Biotechnol. Biochem., 71(12), pp. 2927-2933 (2007).

E. Larrucea et al., "Study of the Complexation Behavior of Tenoxicam with Cyclodextrins in Solution: Improved Solubility and Percutaneous Permeability", Drug Development and Industrial Pharmacy, 28(3), pp. 245-252 (2002).

K. Miyake et al., "Improvement of Solubility and Oral Bioavailability of Rutin by Complexation with 2-Hydroxypropyl-b-cyclodextrin", Pharmaceutical Development and Technology, 5(3), pp. 399-407 (2000).

Communications to the Editor, "Esters of N,N-Disubstituted 2-Hydroxyacetamides as a Novel Highly Biolabile Prodrug Type for Carboxylic Acid Agents", Journal of Medicinal Chemistry, 30(3), pp. 451-454 (1987).

A. Casaschi et al., "The Chalcone Xanthohumol Inhibits Triglyceride and Apolipoprotein B Secretion in HepG2 Cells", The Journal of Nutrition, pp. 1340-1346 (2004).

B. Vanhoecke et al., "Antiinvasive effect of xanthohumol, a prenylated chalcone present in hops (*Humulus lupulus* L.) and beer", Int. J. Cancer, vol. 117, pp. 889-895 (2005).

K. Goto et al., "Enhanced antitumor activity of xanthohumol, a diacylglycerol acyltransferase inhibitor, under hypoxia", Cancer Letters 219, pp. 215-222 (2005).

C.Gerhauser et al., "Cancer Chemopreventive Activity of Xanthohumol, a Natural Product Derived from Hop" Molecular Cancer Therapeutics, vol. 1, pp. 959-969 (2002).

Japenese Office Action dated Oct. 31, 2013 for JP Appln. No. 2010-548746.

Supplementary European Search Report for EP 09 71 5696 (PCT/US2009/001301).

EPO Communication Pursuant to Article 94(3) Re EP Appln. 09 715 692.2.

* cited by examiner

COMPOSITIONS CONTAINING XANTHOHUMOL-CYCLODEXTRIN COMPLEXES

CROSS-REFERENCE TO RELATED APPLICATIONS

This application is the U.S. national phase application, pursuant to 35 U.S.C. §371, of PCT International Application No. PCT/US2009/001301, filed Feb. 26, 2009, which claims the benefit of U.S. Provisional Patent Applications No. 61/031,762, filed Feb. 27, 2008, the contents of which are incorporated herein by reference in their entirety.

BACKGROUND OF THE INVENTION

Xanthohumol, a hop flavonoid, exhibits a broad range of bioactivities. For example, it is an anti-oxidant and is useful for treating diseases associated with oxidative stress, such as cancer. In another example, xanthohumol ameliorates diabetes and dyslipidaemia.

Current xanthohumol-containing products have at least two disadvantages. First, the bioavailability of xanthohumol in these products is very poor due to its low water-solubility. Second, xanthohumol products often contain a substantial amount of isoxanthohumol, which results from the breakdown of xanthohumol during preparation or storage of xanthohumol-containing products. The presence of isoxanthohumol is disadvantageous because it possesses undesirable estrogenic activity.

Thus, there is a need to develop a new product that contains highly bioavailable xanthohumol and little or no isoxanthohumol.

SUMMARY OF THE INVENTION

As described below, the invention provides compositions and methods featuring a water soluble xanthohumol/cyclodextrin complex having increased stability relative to xanthohumol alone.

In one aspect, the invention generally features a composition comprising a xanthohumol (e.g., 3'-[3,3-dimethyl allyl]-2',4',4-trihydroxy-6'-methoxychalcone, a prenylated chalcone derived from hops, xanthoangelol, xanthoangelol F, 4-hydroxyderricin, 4-O-methylxanthohumol, isobavachalcone, xanthoangelol H, xanthogalenol, desmethoxyxanthohumol, 5'-prenylxanthohumol, tetrahydroxanthohumol, 2',4', 6',4-terahydroxy-3'-C-geranylchalcone, dehydrocycloxanthohumol, 4-O-5'-C-diphenylxanthohumol, 4'-O-methylxanthohumol, and a xanthohumol metabolite or derivative), and a cyclodextrin (e.g., alpha-cyclodextrin, beta-cyclodextrin, gamma-cyclodextrin, hydroxypropyl-beta-cyclodextrin, sulfobutyl ether-beta-cyclodextrin, heptakis(2,6-di-O-methyl)-beta cyclodextrin, $C_{1-24}$-alkyl-gamma-cyclodextrin, and $C_{1-24}$-hydroxyalkyl-gamma-cyclodextrin), wherein the xanthohumol and the cyclodextrin form a complex.

In another aspect, the invention provides a method of preparing a xanthohumol/cyclodextrin complex, comprising combining xanthohumol and cyclodextrin and adjusting the pH to 10-12, thereby providing for xanthohumol/cyclodextrin complex formation. In one embodiment, the method further involves recovering the complex (e.g., by re-adjusting the pH to 6-9 to allow precipitation of the xanthohumol/cyclodextrin complex). In one embodiment, the xanthohumol is present in spent hops or a hops extract. In another embodiment, the method further involves removing insoluble materials from the mixture either before or after pH adjustment. In yet another embodiment, the xanthohumol and cyclodextrin are present in water or a water-miscible solvent that is any one or more of methanol, ethanol, propanol, isopropanol, glycerine, ethylene, glycol, and polyethylene glycol (PEG). In one embodiment, the water-miscible solvent is ethanol. In yet another embodiment, cyclodextrin selectively forms a complex with xanthohumol. In yet another embodiment, cyclodextrin fails to form a complex with isoxanthohumol or forms only a negligible amount (e.g., less than about 10%, 7%, 5%, 3%, 2%, 1%, 0.5% of the composition by weight) of a cyclolextrin/isoxanthohumol complex.

In another aspect, the invention provides a composition comprising a xanthohumol/cyclodextrin complex obtained by the method of a previous aspect or any method delineated herein.

In another aspect, the invention provides a method of treating a disease, comprising administering to a subject in need thereof an effective amount of a composition of a previous aspect or a composition delineated herein, wherein the disease is cancer, inflammatory disease, viral infection, skin disorder, learning and memory disorder, obesity, type II diabetes, age-related macular degeneration, cardiovascular disease, or dyslipidaemia.

In another aspect, the invention provides a method of lowering cholesterol levels in a subject, comprising administering to the subject an effective amount of a composition of a previous aspect or a composition delineated herein.

In another aspect, the invention provides a method of treating a disease mediated by Acyl-CoA diacylglycerol acyltransferase (DGAT), Acyl-CoA cholesterol acyltransferase (ACAT), or VEGF, comprising administering to a subject in need thereof an effective amount of a composition of a previous aspect or a composition delineated herein.

In another aspect, the invention provides a pharmaceutical composition comprising an effective amount of a xanthohumol/cyclodextrin complex of a previous aspect or a composition delineated herein in a pharmaceutically acceptable excipient. In one embodiment, an effective amount of the xanthohumol/cyclodextrin complex is between about 0.5 μg to 200 mg (0.5, 1, 2, 3, 4, 5, 6, 7, 8, 9, 10, 100, 250, 500 μg, or 1, 5, 10, 25, 50, 100, 125, 150, 200 mg) per dose per day. In one embodiment, an effective amount of a xanthohumol/cyclodextrin complex is 0.001 to 3.0% or more by weight of the composition, wherein the bottom of the range is a number between 0.001 and 2.9%, and the top of the range is between 0.002 and 3.0%, and the range comprises each number in between. In another embodiment, the composition has increased oral availability relative to xanthohumol alone.

In another aspect, the invention provides a nutraceutical composition comprising a xanthohumol/cyclodextrin complex in an acceptable carrier.

In yet another aspect, the invention provides a non-alcoholic food product comprising a xanthohumol/cyclodextrin complex. In one embodiment, the food product is selected from the group consisting of milk, tea, soft drink, juice, coffee, seasoning, cereal, water, yogurt, cookies, chewing gum, chocolate, and soup.

In another aspect, the invention provides a dietary supplement comprising a xanthohumol/cyclodextrin complex.

In another aspect, the invention provides a pharmaceutical pack comprising a xanthohumol/cyclodextrin complex formulated in individual dosage amounts.

In various embodiments of any previous aspect or any aspect of the invention delineated herein xanthohumol is any one or more of 3'-[3,3-dimethyl allyl]-2',4',4-trihydroxy-6'-methoxychalcone, a prenylated chalcone derived from hops, xanthoangelol, xanthoangelol F, 4-hydroxyderricin, 4-O-methylxanthohumol, isobavachalcone, xanthoangelol H, xanthogalenol, desmethoxyxanthohumol, 5'-prenylxanthohumol, tetrahydroxanthohumol, 2',4',6',4-terahydroxy-3'-C-geranylchalcone, dehydrocycloxanthohumol, 4-O-5'-C-diphenylxanthohumol, 4'-O-methylxanthohumol, and a xanthohumol metabolite or derivative or degradation product, and a cyclodextrin is any one or more of alpha-cyclodextrin, beta-cyclodextrin, gamma-cyclodextrin, hydroxypropyl-beta-cyclodextrin, sulfobutyl ether-beta-cyclodextrin, heptakis(2,6-di-O-methyl)-beta cyclodextrin, $C_{1-24}$-alkyl-gamma-cyclodextrin, and $C_{1-24}$-hydroxyalkyl-gamma-cyclodextrin. In other embodiments of the an invention delineated herein the xanthohumol:cyclodextrin molar ratio is 2:1, 1:1, 1:2, 1:3, 1:4, 1:5, 1:6, 1:7, 1:8, or 1:10 in the complex. In still other embodiments of the an invention delineated herein the cyclodextrin:xanthohumol molar ratio is 2:1, 1:1, 1:2, 1:3, 1:4, 1:5, 1:6, 1:7, 1:8, or 1:10 in the complex. In one embodiment, the xanthohumol:cyclodextrin molar ratio is 1:2 or 1:1. In yet another embodiment, the xanthohumol:cyclodextrin molar ratio is 1:3. In still other embodiments, the composition comprises or consists essentially of 0.01-30%, 0.05-20%, or 0.1-10% by weight xanthohumol or a xanthohumol/cyclodextrin complex. In still other embodiments, a composition delineated herein further contains a pharmaceutically acceptable or edible carrier. In still other embodiments of any aspect of the invention delineated herein, the xanthohumol/cyclodextrin complex is at least about 5-10 (e.g., 5, 6, 7, 8, 9, 10) times more soluble in water than xanthohumol alone. In still other embodiments, the composition comprises less than about 3-5% (e.g., 3, 4, 5%) isoxanthohumol after 3-6 months storage. In another embodiment, the composition comprises less than about 2% isoxanthohumol after 3-6 months storage. In still other embodiments, the cyclodextrin selectively forms a complex with xanthohumol. In one embodiment, a composition of the invention is devoid of a cyclodextrin/isoxanthohumol complex or comprises less than about 10% of a cyclodextrin/isoxanthohumol complex. In one embodiment, the xanthohumol is present in spent hops or a hops extract.

The composition of this invention can be used for treating diseases associated with abnormal lipid or glucose metabolism (e.g., obesity, type II diabetes, cardiovascular disease, or dyslipidaemia) or diseases associated with the NF-kappaB/Akt pathway (e.g., inflammatory disease and cancer). The treatment is performed by administering to a subject in need thereof an effective amount of the composition. The term "treating" as used herein refers to the application or administration of a composition including active agents to a subject, who has one or more of the above-mentioned diseases, a symptom of the diseases, or a predisposition toward the diseases, with the purpose to cure, heal, alleviate, relieve, alter, remedy, ameliorate, improve, or affect the disease, the symptoms of the diseases, or the predisposition toward the diseases. "An effective amount" as used herein refers to the amount of an active agent, which, upon administration with one or more other active agents, if any, to a subject in need thereof, is required to confer therapeutic effect on the subject. An effective amount varies, as recognized by those skilled in the art, depending on route of administration, excipient usage, and the co-usage with other active agents.

This composition can also be used for the manufacture of a medicament for the treatment of the aforementioned diseases.

Also within the scope of this invention is a method for preparing the xanthohumol-cyclodextrin complex described above. This method includes the following steps: (1) mixing a substance (e.g., spent hops) that contains a xanthohumol compound, a cyclodextrin compound, and water or a water-miscible solvent to form a mixture; (2) adjusting the pH of the mixture to 10-12 to allow formation of a complex of the xanthohumol compound and the cyclodextrin compound; and (3) recovering the complex from the mixture. If the mixture contains water-insoluble materials, they can be removed from the mixture either before or after adjusting its pH to 10-12. In one example, the complex is recovered from the mixture (after removal of insoluble materials, if any) by re-adjusting the pH of the mixture to 6-9 to allow precipitation of the complex and then collecting the precipitated complex. The water-miscible solvent used in this method can be methanol, ethanol, propanol, isopropanol, glycerine, ethylene, glycol, and polyethylene glycol. The invention includes compositions made by the processes delineated herein, and their use to treat or prevent conditions or disease (or symptoms thereof) delineated herein.

The invention provides water soluble xanthohumol/cyclodextrin complexes having enhanced stability. Other features and advantages of the invention will be apparent from the detailed description, and from the claims.

Definitions

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "complex" is meant physically associate. Association in a complex can be mediated, for example, by attractions between molecules of different charge, or by hydrophobic or hydrophilic interactions.

By "cyclodextrin" is meant a cyclic oligosaccharide comprising glucose monomers arranged in a toroidal shape or a derivative thereof. Exemplary cyclodextrins include α, β, and γ cyclodextrin, hydroxypropyl-beta-cyclodextrin, sulfobutyl ether-beta-cyclodextrin, heptakis(2,6-di-O-methyl)-beta cyclodextrin, $C_{1-24}$-alkyl-gamma-cyclodextrin, and $C_{1-24}$-hydroxyalkyl-gamma-cyclodextrin.

"Detect" refers to identifying the presence, absence or amount of the object to be detected.

By "disease" is meant any condition or disorder that damages or interferes with the normal function of a cell, tissue, or organ. Examples of diseases include bacterial invasion or colonization of a host cell.

By "effective amount" is meant the amount required to ameliorate the symptoms of a disease relative to an untreated patient. The effective amount of active compound(s) used to practice the present invention for therapeutic treatment of a neurodegenerative disease varies depending upon the manner of administration, the age, body weight, and general health of the subject. Ultimately, the attending physician or veterinarian will decide the appropriate amount and dosage regimen. Such amount is referred to as an "effective" amount.

By "isolated" is meant separated from components that naturally accompany the isolated agent. For example, a compound is isolated when it is at least 60%, by weight, free from the proteins and naturally-occurring organic molecules with which it is naturally associated. Preferably, the preparation is at least 75%, more preferably at least 90%, and most preferably at least 99%, by weight, a compound of the invention. An isolated compound of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "metabolite" is meant the product of metabolic activity.

As used herein, "obtaining" as in "obtaining an agent" includes synthesizing, purchasing, or otherwise acquiring the agent.

By "reference" is meant a standard or control condition.

By "therapeutic composition" is meant a material that is used to ameliorate or treat a disease or disorder.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

By "xanthohumol" is meant a prenylated chalcone derived from hops or a derivative thereof. Exemplary xanthohumols include but are not limited to 3'-[3,3-dimethyl allyl]-2',4',4-trihydroxy-6'-methoxychalcone), xanthoangelol, xanthoangelol F, 4-hydroxyderricin, 4-O-methylxanthohumol, isobavachalcone, xanthoangelol H, xanthogalenol, desmethoxyxanthohumol, 5'-prenylxanthohumol, tetrahydroxanthohumol, 2',4',6',4-terahydroxy-3'-C-geranylchalcone, dehydrocycloxanthohumol, 4-O-5'-C-diphenylxanthohumol, 4'-O-methylxanthohumol, and xanthohumol degradation products.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

DETAILED DESCRIPTION OF THE INVENTION

The invention generally features compositions and methods featuring xanthohumol-cyclodextrin complexes.

The invention is based, at least in part, on the unexpected discoveries that cyclodextrin selectively complexes with xanthohumol, but not isoxanthohumol, and that the xanthohumol/cyclodextrin complex is highly water-soluble and less likely to convert to isoxanthohumol than xanthohumol alone. In this complex (a "host-guest complex"), one or more (e.g., 1, 2, 3, 4) molecules of cyclodextrin form a toroid structure (i.e., a hollow truncated cone having an interior hydrophobic cavity) comprising one or more molecules (e.g., 1, 2, 3, 4) of xanthohumol.

Xanthohumol

Xanthohumol (3'-[3,3-dimethyl allyl]-2',4',4-trihydroxy-6'-methoxychalcone) is a prenylated chalcone derived from hops (*Humulus lupulus* L.), specifically the female flowers of the hop plant, which are used in the brewing industry to add flavor and bitterness to beer. Xanthohumol and related prenylated flavonoids (e.g., 2',4'6',4-tetrahydroxy-3'-prenylchalcone; 2',4',6',4-tetrahydroxy-3' geranylchalcone; dehydrocycloxanthohumol; isoxanthohumol), have a variety of biological activities that indicate that such compounds can act as chemopreventive or chemotherapeutic agents. For example, xanthohumol has anti-oxidant activity (Gerhauser, et al., Molecular Cancer Therapeutics 1:959-969, 2002), anti-proliferative activity (Miranda et al., Food Chem. Toxicol. 37:271-85; 1999; Goto et al., Cancer Letters 219:215-22; Gerhauser, et al., Molecular Cancer Therapeutics 1:959-969, 2002), antiestrogenic activity (Gerhauser, et al., Molecular Cancer Therapeutics 1:959-969, 2002), anti-inflammatory activity (Gerhauser, et al., Molecular Cancer Therapeutics 1:959-969, 2002), and cytotoxic activities (Miranda et al., Food Chem. Toxicol. 37:271-85; 1999). In addition, xanthohumol is reported to inhibit diacylglycerol acyltransferase (Tabata et al., Phytochemistry 46:683-687, 1997).

Xanthohumol isomerizes to form isoxanthohumol, particularly when compositions containing xanthohumol are heated or stored. As reported herein, to reduce susceptibility to isomerization, xanthohumol may be complexed with cyclodextrin.

Cyclodextrin

Figure 1A:
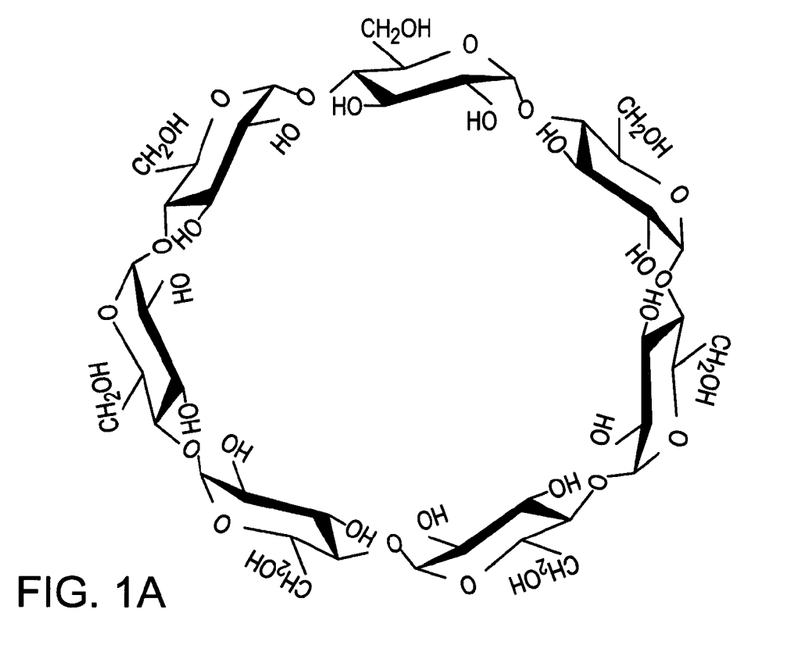
FIGS. 1A and 1B are schematic diagrams showing the structure of exemplary cyclodextrins.
Figure 1B:
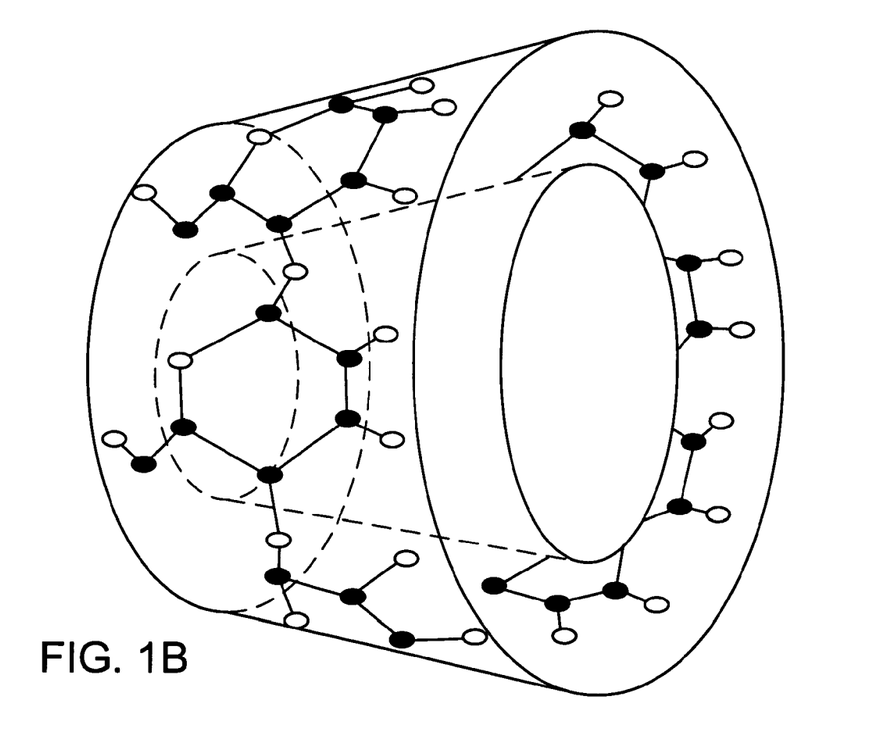

The enzymatic degradation of starch by cyclodextrin-glycosyltransferase (CGT) produces cyclic oligomers, termed cyclodextrins. Cyclodextrins are non-reducing, crystalline, water soluble, cyclic oligosaccharides that consist of glucose monomers arranged in a toroidal shape, which forms a tight conical cylinder having a hydrophilic exterior (due to the presence of hydroxyl radicals) and a hydrophobic interior cavity (FIGS. 1A and 1B). The hydrophobic internal cavity provides for the formation of inclusion complexes with a variety of "guest" hydrophobic molecules (e.g. aromatics, alcohols, halides, fatty acids, esters). Naturally occurring cyclodextrins include α (6 sugar units), β (7 sugar units) and γ (8 sugar units) cyclodextrins.

Cyclodextrins can be modified by various procedures, such as substituting one or more hydrogen atoms in the primary and/or secondary hydroxyl groups. Chemically modified cyclodextrins exhibit substantially increased aqueous solubility while retaining the ability to form inclusion complexes. Cyclodextrin inclusion is a molecular phenomenon in which at least one guest molecule interacts with the cavity of a cyclodextrin molecule to form a stable association. Depending on the molecular weight of the guest, more than one guest molecule may fit into the cavity. Likewise, high molecular weight molecules may bind more than one Cyclodextrin molecule. Therefore a 1 to 1 molar ratio between the guest and the cyclodextrin may not be achieved. Cyclodextrins form inclusion complexes with a broad range hydrophobic molecules. Complex formation may enhance the aqueous solubility of poorly soluble compounds and enhance the stability of agents susceptible to deterioration.

Xanthohumol/Cyclodextrin Complexes

Xanthohumol/cyclodextrin complexes can be prepared as described herein. Briefly, a composition (e.g., a hop extract or spent hops) comprising xanthohumol is mixed with a cyclodextrin and water or a water miscible solvent to form a mixture. The pH of the mixture is adjusted to 10-12 providing for complex formation between the cyclodextrin and the xanthohumol. The complex is recovered using any method known in the art, such as by collecting the mixture containing the complex or spray-drying the mixture to obtain a complex-containing powder. In one embodiment, insoluble materials are removed, and the mixture containing the complex is acidified to reach a pH value of 6-9, providing for complex precipitation. The mixture is then maintained at a suitable temperature (e.g., room temperature) for a sufficient period of time (e.g., 2 hr, 6 hr, or 12 hr) to provide for optimal precipitation. The precipitated complex is then collected by any means known in the art, such as centrifugation or filtration. If desired, the precipitate is washed with suitable solvents and dried.

In the method described above, when spent hops are used as the substance containing a xanthohumol compound, they are dispersed in water together with a cyclodextrin compound to form a mixture. The water-insoluble materials present in the spent hops are removed by any means known in the art, such as filtration or centrifugation. This step may be carried out before or after the pH is adjusted to 10-12. When a xanthohumol compound and a cyclodextrin compound are used as the starting materials in the aforementioned method, they are dissolved together in water or a water miscible solvent to form a solution. Alternatively, the xanthohumol compound is dissolved in water or a water miscible solvent first and then mixed with an aqueous solution containing the cyclodextrin compound to form a solution. The solution is then adjusted to pH 10-12. Xanthohumol/cyclodextrin compounds are then precipitated as described above.

As described herein, cyclodextrin selectively forms a complex with xanthohumol, but fails to form a complex with isoxanthohumol or forms a reduced level of such complexes. For example, a composition of the invention comprises less than about 10%, 7%, 5%, 3%, 1%, 0.5% cyclodextrin/isoxanthohumol complexes.

Without being bound by theory, a xanthohumol-containing composition is likely to be useful an antioxidant. Xanthohumol is a well-known antioxidant. See e.g., Stevens et al., *Chem. Res. Toxicol.*, 16(10):1277-1286 (2003). In one embodiment, a xanthohumol/cyclodextrin complex of the invention is useful for the treatment of oxidative stress-related diseases (e.g., cancer, aging, atherosclerosis, ischemic injury, inflammation, and neurodegenerative diseases (e.g., Parkinson's and Alzheimer's)).

Xanthohumol has also been found to lower levels of plasma glucose and hepatic triglyceride in mice. See Nozawa, *Biochemical and Biophysical Research Communications*, 336 (3):754-761 (2005). In addition, xanthohumol inhibits both acyl CoA:diacylglycerol acyltransferase (DGAT), which is involved in triglyceride synthesis, and acyl-coenzyme A cholesterol acyl transferase (ACAT), which is involved in cholesterol esterification. See Casaschi et al., *J. Nutr.*, 134(6): 1340-1346, 2004; and US20070042063A1. Thus, xanthohumol can be used to treat diseases associated with abnormal lipid/glucose metabolism, or with DGAT/ACAT, e.g., obesity, type II diabetes, cardiovascular disease, and dyslipidaemia. It can also be used to lower cholesterol level in a subject.

Xanthohumol also suppresses both the NF-kappaB and Akt pathways, thereby interfering with angiogenesis. See Albini et al., *FASEB J.*, 20(3):527-529, 2006. Xanthohumol is a potential anti-angiogenesis agent useful in treating tumors, in particular, solid tumors. Because xanthohumol inhibits NF-kappaB, which functions in generating an immune response, xanthohumol is also useful for the treatment of immune cell-mediated disorders, such as inflammatory disease.

Finally, xanthohumol is useful for the treatment of viral infections (see Antiviral Res. 2004 January; 61(1):57-62; and Antiviral Res. 2004 December; 64(3):189-94), skin disorders (e.g., acne and skin aging; See Int J Cancer. 2005 Dec. 20; 117(6):889-95) and learning and memory disorders (see US 2004 0219238A1).

Accordingly, the present invention provides methods of treating disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a disease or disorder or symptom thereof. The method includes the step of administering to the mammal a therapeutic amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which a metabolic disorder or oxidative damage may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with oxidative stress, abnormal lipid/glucose metabolism, immune cell-mediated disorder, viral infection, skin disorder, or learning and memory disorders in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Hop Derivatives

A hop derivative is a compound that occurs naturally in a hop plant (*Humulus lupulus*) or is chemically derived (either through natural biosynthetic procesess (e.g., living organism metabolism (e.g., mammal, plant, bacteria)) or by synthetic processes using human intervention (e.g., chemical synthesis). Compositions of the invention include one or more compounds derived from hops. Of particular interest are hop polyphenols, including but not limited phenolic acids, prenylated chalcones, flavonoids, catechins, proanthocyanidins, xanthohumol, and isoxanthohumol. When hops are extracted with pure ethanol, methanol, or ethanol or methanol/water mixtures of a high ethanol content of (e.g., 90% by weight of ethanol), virtually all relevant hop constituents, including xanthohumol, are extracted. See, for example, EP-B1-0 057 435. After removing the solvent (ethanol, methanol, or mixtures thereof), a crude extract is obtained. This crude extract can be separated into a polar fraction and a non-polar fraction containing the xanthohumol. Phase separation can be accelerated and/or completed by centrifuging the crude extract. The non-polar fraction containing the xanthohumol is obtained after phase separation. Approximately 80% of the constituents may be extracted from the ethanol extract using supercritical $CO_2$, for example, as described in EP-A1-0 320 813. Alternative methods for extracting xanthohumol are provided, for example, at U.S. Pat. No. 6,867,332. Plant extracts are often used for the purification of compounds from plants (e.g., hops). An extract can be prepared by drying and subsequently cutting or grinding the dried material. The term "extract" refers to a concentrated preparation of the essential constituents of a plant, such as hops. Typically, an extract is prepared by drying and powderizing the plant. Optionally, the plant, the dried plant or the powderized plant may be boiled in solution. The extract may be used in liquid form, or it may be mixed with other liquid or solid herbal extracts. Alternatively, the extract may be obtained by further precipitating solid extracts from the liquid form. The extraction process may then be performed with the help of an appropriate choice of solvent, typically ethanol/water mixture, methanol, butanol, iso-butanol, acetone, hexane, petroleum ether or other organic solvents by means of maceration, percolation, repercolation, counter-current extraction, turbo-extraction, or by carbon-dioxide supercritical (temperature/pressure) extraction. The extract may then be further evaporated and thus concentrated to yield by means of air drying, spray drying, vacuum oven drying, fluid-bed drying or freeze-drying, the extract product.

Numerous methods are available for the chemical synthesis of xanthohumol or cyclodextrin. Such compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); L. Paquette, ed., Encyclopedia of Reagents for Organic Synthesis, John Wiley and Sons (1995); and M. Verzele and D. De Keukeleire, Chemistry and Analysis of Hop and Beer Bitter Acids, Elsevier: Amsterdam (1991), and subsequent editions thereof. Chemically synthesized xanthohumol can be separated from a reaction mixture and further purified by a method such as column chromatography, high pressure liquid chromatography, or recrystallization. As can be appreciated by the skilled artisan, further methods of synthesizing the compounds herein will be evident to those of ordinary skill in the art. Additionally, the various synthetic steps may be performed in an alternate sequence or order to give the desired compounds.

The compounds of this invention may contain one or more asymmetric centers and thus occur as racemates and racemic mixtures, single enantiomers, enantiomer mixtures, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention. As used herein, the compounds of this invention, including the compounds of formulae described herein, are defined to include derivatives. Derivatives include compounds of the invention that are modified by appending appropriate functionalities to enhance desired properties.

Acceptable salts of the compounds of this invention include those derived from acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic acid, may be employed in the preparation of salts useful as intermediates in obtaining the compounds of the invention and their acceptable acid addition salts. Salts derived from appropriate bases include alkali metal (e.g., sodium), alkaline earth metal (e.g., magnesium), ammonium and $N\text{-(alkyl)}_4^+$ salts. This invention also envisions the quaternization of any basic nitrogen-containing groups of the compounds disclosed herein. Water or oil-soluble or dispersible products may be obtained by such quaternization.

The ratio of xanthohumol to cyclodextrin ranges between about 1:1 and 1:10. In another embodiment, the ratio of xanthohumol to cyclodextrin ranges between about 10:1 and 1:1. In other embodiments of these ratios include 1:2, 1:3, 1:4, 1:5, 1:6, 1:7, 1:8, 1:9, and 1:10. In preferred embodiments, a preparation of the invention includes between 1 and 95% (e.g., 1, 2, 3, 4, 5, 6, 7, 8, 9, 10, 25, 75, 80, 90, or 95%) of a xanthohumol/cyclodextrin complex in a carrier or diluent. Alternatively, such preparations contain from about 20% to about 80% of a xanthohumol/cyclodextrin complex. Compositions containing xanthohumol are manufactured by ordinary methods. Xanthohumol/cyclodextrin complexes suitable for addition to products can be formulated as ordinary tablets, capsules, solids, liquids, emulsions, slurries, fine granules or powders, which are suitable for administration to products during their preparation, following preparation but prior to storage, or at any time prior to their sale to a vendor or consumer. Lower or higher amounts than those recited above may be required. Specific dosage and treatment regimens are determined empirically as described herein.

Compound Derivatives

Compositions of the invention include xanthohumol/cyclodextrin complexes. These compositions include both the compounds themselves and their derivatives (e.g., sugar derivatives, metabolic derivatives, prodrugs, derivatives by isomerization, oxidization product, and reduction product). Such derivatives may be naturally occurring or synthetic derivatives. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30, 451-454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development;* 2 ed.; Overseas Publ.: Amsterdam, 1996; pp 351-385; Pitman, I. H. *Medicinal Research Reviews* 1981, 1, 189-214; Sinkula, A. A.; Yalkowsky. *Journal of Pharmaceutical Sciences* 1975, 64, 181-210; Verbiscar, A. J.; Abood, L. G *Journal of Medicinal Chemistry* 1970, 13, 1176-1179; Stella, V. J.; Himmelstein, K. J. *Journal of Medicinal Chemistry* 1980, 23, 1275-1282; Bodor, N.; Kaminski, J. J. *Annual Reports in Medicinal Chemistry* 1987, 22, 303-313.

The compounds of this invention may be modified by appending appropriate functionalities to enhance selective biological properties. Such modifications are known in the art and include those which increase biological penetration into a given biological compartment (e.g., blood, lymphatic system, nervous system), increase oral availability, increase solubility to allow administration by injection, alter metabolism and alter rate of excretion.

Nutraceutical Formulations

Nutraceutical compositions are preparations that include compounds of the invention in combination with natural ingredients and supplements that promote good health. Preferably, such nutraceuticals are useful as chemopreventive or chemotherapeutics based on their activity in enhancing health. The combinations provided by the invention contain xanthohumol/cyclodextrin complexes. Information about numerous plants and herbs that have been used to prepare nutraceutical compositions has been compiled and is available in publications including the German Commission E Monographs (by German Federal Institute for Drugs and Medical Devices Commission E), Botanical Safety Handbook Guide for Safe Use and Labeling for Herbs in Commerce, editor M. McGuffin, and HerbalGram, a quarterly publication of the American Botanical Council, which references numerous clinical trials that have been performed using nutraceuticals.

The actions of nutraceutical compositions may be fast or/and short-term or may help achieve long-term health objectives. Nutraceutical compositions may comprise dried and ground plant (e.g., hops) tissue or extracts from these tissues in an acceptable medium as a natural approach for treatment or prevention of a disease described herein. The nutraceutical compositions may be contained in an edible material, for example, as a dietary supplement or a pharmaceutical formulation. As a dietary supplement, additional nutrients, such as vitamins, minerals or amino acids may be included. The composition can also be a drink or a food product, e.g., tea, soft drink, juice, milk, coffee, cookie, cereal, chocolate, and snack bar. If desired, the composition can be sweetened by adding a sweetener such as sorbitol, maltitol, hydrogenated glucose syrup and hydrogenated starch hydrolyzate, high fructose corn syrup, cane sugar, beet sugar, pectin, or sucralose.

In another example, the composition of this invention, containing an edible carrier, is a component of a food product (e.g., yogurt, milk, or soy milk) or a food supplement (e.g., a nutrient supply or an herbal product). Examples of an edible carrier include starch, cyclodextrin, maltodextrin, methylcellulose, carbonmethoxy cellulose, xanthan gum, and aqueous solutions thereof. Such food products can be prepared by methods well known in the food industry. As used herein, the term "food" broadly refers to any kinds of liquid and solid/semi-solid materials that are used for nourishing humans and animals, for sustaining normal or accelerated growth, or for maintaining stamina or alertness.

The composition of this invention, containing xanthohumol, can be used to treat a variety of diseases and disorders, e.g., cancer, inflammatory disease, age-related macular degeneration, or cardiovascular disease.

A nutraceutical comprising a composition of this invention can be in the form of a solution. Typically, the composition of the invention is provided in a medium, such as a buffer, a solvent, a diluent, an inert carrier, an oil, or a crème. In one embodiment, the composition is present in an aqueous solution that optionally contains a non-aqueous co-solvent, such as an alcohol. The composition can also be in the form of powder, paste, jelly, capsule, or tablet. Lactose and corn starch are commonly used as diluents for capsules and as carriers for tablets. Lubricating agents, such as magnesium stearate, are typically added to form tablets.

Therapeutics

Therapeutic compounds and therapeutic combinations comprising xanthohumol/cyclodextrin complexes are administered in an effective amount. In certain embodiments, compounds of the invention, such as those described herein, are administered at dosage levels of about 0.0001 to 4.0 grams once per day (or multiple doses per day in divided doses) for adults. Thus, in certain embodiments of this invention, a compound herein is administered at a dosage of any dosage range in which the low end of the range is any amount between 0.1 mg/day and 400 mg/day and the upper end of the range is any amount between 1 mg/day and 4000 mg/day (e.g., 5 mg/day and 100 mg/day, 150 mg/day and 500 mg/day, 300 mg/day-1000 mg/d (oral)). In other embodiments, a compound herein, is administered at a dosage range in which the low end of the range is any amount between 0.1 mg/kg/day and 90 mg/kg/day and the upper end of the range is any amount between 1 mg/kg/day and 100 mg/kg/day (e.g., 0.5 mg/kg/day and 2 mg/kg/day, 5 mg/kg/day and 20 mg/kg/day). Preferably, a combination of the invention is administered at a dosage of 1.5 mg/kg/day, 15 mg/kg/day, or 30 mg/kg/day. The dosing interval can be adjusted according to the needs of individual patients. For longer intervals of administration, extended release or depot formulations can be used.

Formulation of Pharmaceutical Compositions

The administration of a compound for the treatment of a disease or disorder described herein may be by any suitable means that results in a concentration of the therapeutic that, combined with other components, is effective in ameliorating, reducing, or stabilizing a disease or disorder. The xanthohumol/cyclodextrin complexes may be contained in any appropriate amount in any suitable carrier substance, and is generally present in an amount of 1-95% by weight of the total weight of the composition. Preferably, the composition is provided in a dosage form that is suitable for oral administration. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active compound substantially immediately upon administration or at any predetermined time or time period after administration. The latter types of compositions are generally known as controlled release formulations. For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Solid Dosage Forms for Oral Use

Formulations for oral use include tablets containing the active ingredient(s) (e.g., xanthohumol/cyclodextrin complexes) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed.

The solid tablet compositions may include a coating adapted to protect the composition from unwanted chemical changes, (e.g., chemical degradation prior to the release of the active therapeutic substance). The coating may be applied on the solid dosage form in a similar manner as that described in Encyclopedia of Pharmaceutical Technology, supra.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the active therapeutic by controlling the dissolution and/or the diffusion of the active substance. Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more therapeutic compounds may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the compound(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Kits

The invention provides kits comprising xanthohumol/cyclodextrin complexes for the treatment or prevention of disease or disorder, or symptoms thereof. In one embodiment, the kit includes a pharmaceutical pack comprising an effective amount of a xanthohumol/cyclodextrin complex. Preferably, the compositions are present in unit dosage form. In some embodiments, the kit comprises a sterile container which contains a therapeutic or prophylactic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired compositions of the invention or combinations thereof are provided together with instructions for administering them to a subject having or at risk of developing a disease or disorder. The instructions will generally include information about the use of the compounds for the treatment or prevention of a disease or disorder. In other embodiments, the instructions include at least one of the following: description of the compound or combination of compounds; dosage schedule and administration for treatment of a disease described herein or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

The following examples are provided to illustrate the invention, not to limit it. Those skilled in the art will understand that the specific constructions provided below may be changed in numerous ways, consistent with the above described invention while retaining the critical properties of the compounds or combinations thereof.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Preparation of Xanthohumol-Cyclodextrin Complex on a 10 ml Scale

Pure xanthohumol (containing >99% xanthohumol by weight) was dissolved in ethanol to form a xanthohumol solution at a concentration of 200 mg/ml. 10 g gamma cyclodextrin (CAVAMAX-W8, food grade, lot no. 80F036, Wacker Chemie, AG) was dissolved in 90 ml water to form an aqueous cyclodextrin solution. After its pH being adjusted to 10.87, the aqueous cyclodextrin solution was mixed with the xanthohumol solution to produce a mixture. The pH of the mixture was adjusted, if necessary, to the range of 10.5-10.9, under which gamma cyclodextrin and xanthohumol form a host-guest complex. $H_2SO_4$ was then added to the mixture to re-adjust its pH to 7.5 and the mixture was kept at room temperature overnight to allow precipitation of the complex. The mixture was subjected to centrifugation for collection of both the precipitated complex and the supernatant thus form. The collected complex was then dried to produce 295 g powder having 17% by weight xanthohumol. The ratio of iso-xanthohumol to xanthohumo is 0.0067 in the powder and is 200 in the supernant. This result indicates that cyclodextrin forms a complex selectively with xanthohumol, but not iso-xanthohumol.

Example 2

Preparation of Xanthohumol-Cyclodextrin Complex on a 100 ml Scale

Xanohop A (a hop extract containing 50% by weight xanthohumol) was dissolved in ethanol (1.25 g Xanohop A per 5 ml ethanol) to form a xanthohumol solution, which was then mixed with an aqueous solution containing 10% gamma cyclodextrin to form a mixture. The pH of the mixture was adjusted to 10.9 to 11.0. After removing some brown precipitates via filtration, $H_2SO_4$ was added to the mixture such that it pH was re-adjusted to 7.9. The mixture was then kept still at room temperature overnight to allow formation of yellowish precipitates. The precipitates were collected by filtration and dried to produce 4.52 g powder, which contained 12% by weight xanthohumol. In the powder, cubic crystals of xanthohumol-gamma cyclodextrin complex were observed under optical microscope. Note that pure xanthohumol forms needle-shaped crystals. The iso-xanthohumol/xanthohumol ratio in the resultant powder was 0.015.

As shown below, the water solubility of xanthohumol contained in the xanthohumol-cyclodextrin complex thus prepared is much higher than pure xanthohumol and xanthohumol in Xanohop A.

Pure xanthohumol (XN), Xanohop A, and xanthohumol-gamma cyclodextrin (XN/gCD) were dispersed in water at a ratio of 1 mg xanthohumol per ml of water. After being sonicated for 5 minutes, the resultant suspensions were centrifuged at 3,000 rpm for 2 minutes or 12,000 rpm for 3 minutes. The supernatants thus formed were collected, diluted (1:10) with methanol, and then injected into HPLC to determine xanthohumol concentrations. Results thus obtained indicate that xanthohumol in XN/gCD complex is about 20 times more soluble in water than pure xanthohumol and about 10 times more soluble in water than Xanohop A (Table 2, below)

TABLE 1

Water-Solubility of Xanthohumol (XN)

|  | Water-solubility of XN (3,000 rpm) | Water-solubility of XN (12,000 rpm) |
|---|---|---|
| Pure XN | 4 ug/ml | 2 ug/ml |
| Xanohop A | 12 ug/ml | 6 ug/ml |
| XN/gCD | 78 ug/ml | 45 ug/ml |

Legend:
Xn denotes xanthohumol;
CD denotes cyclodextrin

Xanohop A (sample 1), XN-cremophore composition (sample 2), and XN/gCD complex (sample 3) were tested for conversion of xanthohumol to isothohumol as follows. Samples 1, 2, and 3 were incubated at 75° C. for 5 days (equivalent to one-month storage at room temperature). The contents of iso-xanthohumol in these samples were determined before and after the incubation.

Before incubation, the contents of iso-xanthohumol (versus 100 mg xanthohumol) in Samples (1) and (2) are 6.5 mg and 7.0 mg, respectively, and that in Sample (3) is only 1.2 mg. After incubation, the contents of iso-xanthohumol in Samples (1), (2), and (3) are 8.5 mg, 28.5 mg, and 2.0 mg, respectively. These results indicate that Sample (3), i.e., xanthohumol-gamma cyclodextrin complex, contains the lowest isoxanhumol contents both before and after one-month storage, compared to Sample (1), i.e., Xanohop A, and Sample (2), i.e., xanthohumol-cremophore composition.

Example 3

Preparation of Xanthohumol-Cyclodextrin Complex Using Spent Hops 10.15 g gamma-cyclodextrin (Cavamax-W8, food grade, batch 80F036) was dissolved in 1000 ml water to form an aqueous gamma-cyclodextrin solution (1% by weight), and the pH value of the solution was adjusted to 11.3 by adding 28.17 g $K_2CO_3$. 100 g spent hop powder (variety H.H., Taurus, corp of 2006, milled) was added to the basic cyclodextrin solution to form a dark brown-colored suspension, the pH of which was around 9.6. $K_2CO_3$ was then added to the suspension to reach a pH value of 9.9. The suspension was agitated at 30-40° C. for one hour and then filtered to obtain an orange/brown colored solution. 24.5 ml 5M $H_2SO_4$ was added to the solution to reach a pH of 6.9, at which a yellow precipitate formed slowly. The solution was kept still at room temperature overnight and the precipitate was then collected by filtration. The collected precipitate was vacuum dried with mild heating to yield a yellow powder (2.05 g). The content of xanthohumol in this powder was 10% by weight and the isoxanthohumol/xanthohumol ratio was less than 0.01.

Example 4

Xanthohumol/Cyclodextrin Complex has Increased Stability

Figure 2:
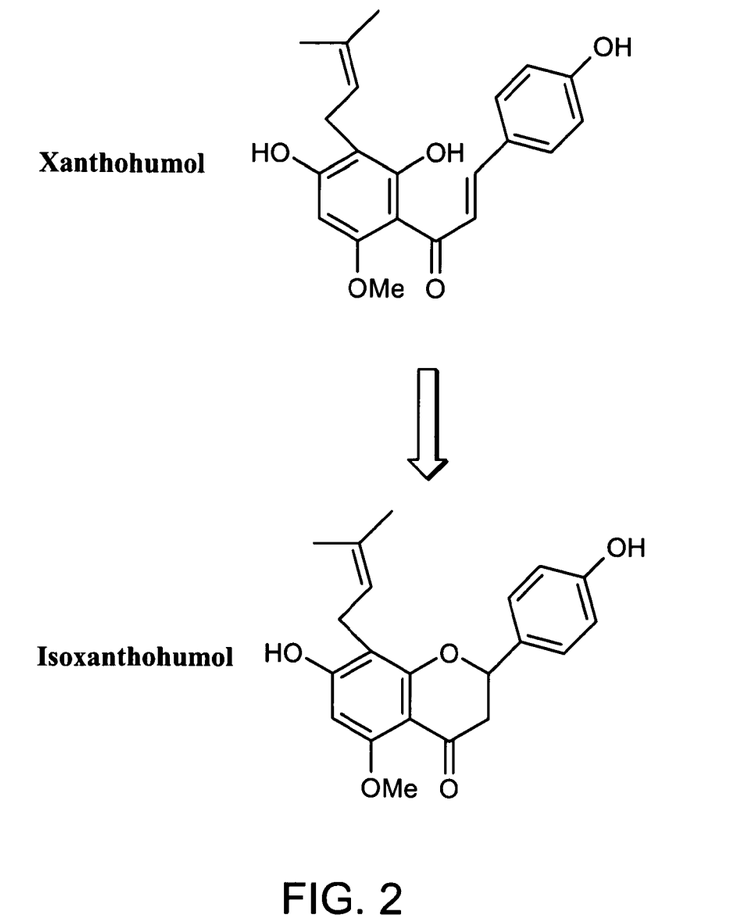
FIG. 2 shows the conversion of xanthohumol to isoxanthohumol.

Xanthohumol/cyclodextrin complex stability was compared with Xanthuhumol alone and Xanthohumol cremophor solution under force conditions (75 C for 120 hours). The main degradation pathway is cyclization to Isoxanthohumol as shown in FIG. 2.

Samples
 1. XN50 (Xanthohumol rich extract: XN50%)
 2. XN/Cremophor (1% Xanthohumol Cremophor)
 3. XN/gCD (Xanthohumol/gamma CD complex, the present invention)

Each sample was incubated at 75 C for 120 hrs (which is equivalent to storage for 6 months at room temperature). Xanthohumol and Isoxanthohumol contents were analyzed by HPLC. Isoxanthohumol is a representative degraded product of Xanthohumol.

After 120 hrs, 5-10% by weight of XN50 (xanthohumol rich extract) had been converted to isoxanthohumol. 7-25% by weight of 1% Xanthohumol Cremophor had been converted to isoxanthohumol. In contrast, only 1%-1.5% of xanthohumol/cyclodextrin had been converted to isoxanthohumol. These results are shown below.
 1. XN 50 5%-10%
 2. XN (cremophor) 7%-25%
 3. XN/CD 1%-1.5%

Clearly, xanthohumol/cyclodextrin has greater stability relative to xanthohumol or xanthohumol (cremophor).

Example 5

Xanthohumol/Cyclodextrin Complexes have Enhanced Oral Absorption

To evaluate oral absorption of Xanthohumol/gamma Cyclodextrin complexes relative to xanthohumol alone and xanthohumol in organic solvent, the following samples were used:

Sample A is pure xanthohumol (XN95%) suspended in water

Sample B is xanthohumol-rich fraction (XN50%) suspended in water.

Sample C is xanthohumol dissolved in Cremophor (organic solvent)

Sample D is the xanthohumol/γ-cyclodextrin complex suspended in water.

Each of the samples was orally administered to Sprature-Dawley rats at 20 mg/kg by oral gavage. Five rats were used in each group. Blood (200 ul) was collected from the saphenous vein at 1, 2, 4, 8 and 24 hours post dose. The blood samples were prepared using a standard blood sample preparation protocol, which follows, and analyzed by HPLC.

Sample Preparation and Analytical Conditions

Blood samples were enzymatically treated. Specifically, 2 ul of 10% dithiothriotol solution, 10 ul of 0.5M acetic acid and 10 ul of B-Glucuronidase/Arylsulfatase (Boehringer Mannheim GmbH, 127 698 or from Sigma/Aldrich G-0876, G-7017) was added into 100 ul of plasma samples. The crude solution of Glucuronidase Type H-2 (Sigma, G-0876) was used without dilution. The mixture is incubated at 37 C for 60 min and then the enzymatic reaction was stopped by addition of 100 ul of 0.01 M oxalic acid. This enzymatic treatment facilitates recovery of Xanthohumol by enzymatic cleavage of major phase I metabolites.

Solid Phase Extraction

After enzymatic incubation, the sample was diluted with 800 ul of 10 mM triethylammonium acetate (TEAA) water (pH=7) and loaded on a Sep Pak Light C18 cartridge column. Sep Pak Light C18 was pre treated with 1 ml of methanol followed by 1 ml of water. TEAA (Fluka, #90357, 1M solution pH=7.0) was diluted to get desired concentration. The SPE column was washed with 2 ml of 5% methanol 10 mM TEAA. Then the sample was eluted with 400 μl of methanol followed by 100 μl of 10 mM TEAA water. After filtration through 0.22 um nylon filter, 100 ul of sample was injected to the HPLC.

HPLC Analytical Conditions

Mobile phase A: 10 mM triethylammonium acetate (TEAA)/water
Mobile phase B: 10 mM TEAA/acetonitrile
Column: C18 column 4.6×250 mm, 5 um, 100A (Shiseido Capcell Pak C18 SG)
Flow rate: 1 ml/min
Gradient: linear gradient from 30% B to 90% B in 20 min, then hold 90% B for 5 min
Injection volume: 100 uL
Column temperature: 35 C
Detection: DAD 370 nm for XN Mobile phase A was prepared by diluting 10 ml of 1M TEAA buffer pH=7 (Fluka, #90357) into 990 ml of HPLC grade water. Mobile phase B was prepared by diluting 10 ml of 1M TEAA buffer pH=7 (Fluka, #90357) into 990 ml of HPLC grade acetonitrile.

Figure 3:
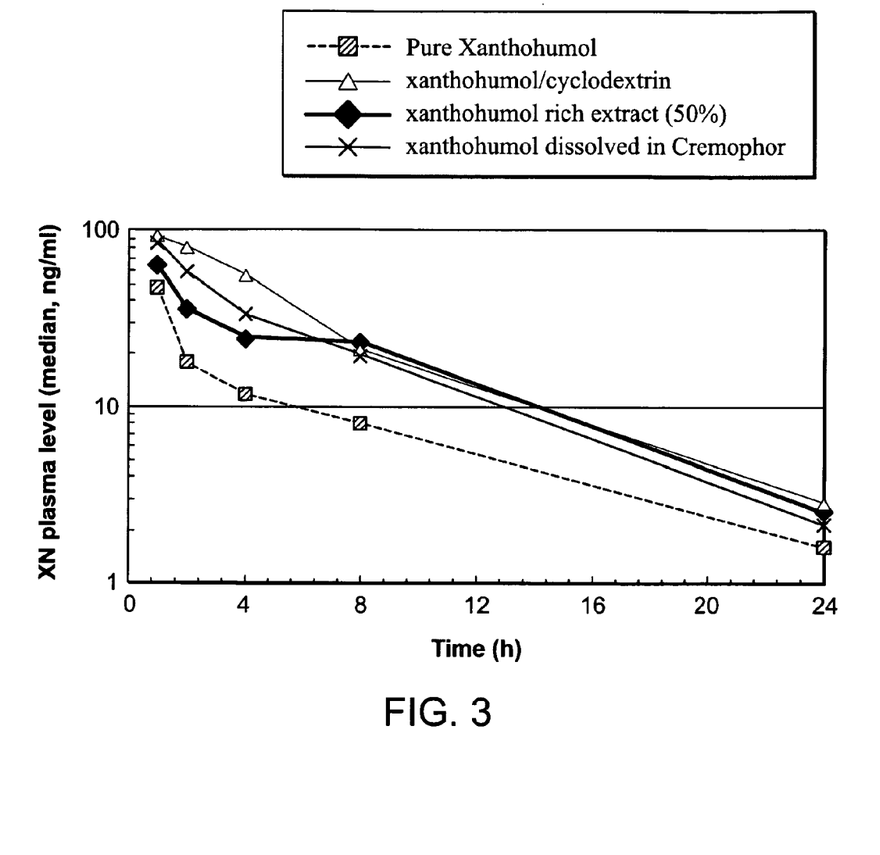
FIG. 3 is a graph showing changes in xanthohumol level following oral administration.

Xanthohumol was absorbed from the intestine to the blood following oral administration. FIG. 3 shows the change in concentration of xanthohumol in rat plasma over 24 hours following oral administration. The vertical axis represents plasma concentration of XN (ng/ml) and the horizontal axis represents the time when the blood sample was taken. The higher the concentration, the higher the oral absorption. The present invention, Sample D (XN/CD complex) showed the highest concentration among the four samples (Cmax and AUC). It is noted that the absorption profile (particularly over 8 hours) is better than that of the liquid sample C (yellow vs. light blue). Pure Xanthohumol (Sample A) was very poorly absorbed following oral administration. In fact, it showed the lowest oral absorption (pink). The oral absorption of xanthohumol rich extract (50%) (Sample B) was better than that of pure Xanthohumol (Sample A) (dark blue). Interestingly, oral absorption of xanthohumol/cyclodextrin complexes was far better than that of xanthohumol alone.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A composition comprising a xanthohumol and a cyclodextrin, wherein the xanthohumol and the cyclodextrin form a complex;
   wherein the xanthohumol is 3'-[3,3-dimethyl allyl]-2',4',4-trihydroxy-6'-methoxychalcone); and
   the cyclodextrin is beta-cyclodextrin.

2. The composition of claim 1, wherein the composition comprises or consists essentially of 0.01-30% by weight of the xanthohumol.

3. The composition of claim 2, wherein the composition comprises or consists essentially of 0.05-20% by weight of the xanthohumol.

4. The composition of claim 3, wherein the composition comprises or consists essentially of 0.1-10% by weight of the xanthohumol.

5. The composition of claim 1, wherein the xanthohumol/cyclodextrin complex is at least about 5-10 times more soluble in water than the xanthohumol alone.

6. The composition of claim 1, wherein the composition comprises less than 3-5% isoxanthohumol after 3-6 months storage.

7. The composition of claim 1, wherein the composition comprises less than 2% isoxanthohumol after 3-6 months storage.

8. The composition of claim 1, wherein the composition is devoid of a cyclodextrin/isoxanthohumol complex or comprises less than 10% of a cyclodextrin/isoxanthohumol complex.

9. The composition of claim 1, wherein the xanthohumol and the cyclodextrin have a molar ratio of 2:1 to 1:4 in the complex.

10. The composition of claim 9, wherein the molar ratio is 1:2.

11. The composition of claim 9, wherein the molar ratio is 1:3.

12. The composition of claim 1, further comprising a pharmaceutically acceptable or edible carrier.

13. A pharmaceutical composition comprising a therapeutically effective amount of the xanthohumol/cyclodextrin complex of claim 1 in a pharmaceutically acceptable excipient.

14. The composition of claim 13, wherein the effective amount of the xanthohumol/cyclodextrin complex is between 0.5 μg to 200 mg per dose per day.

15. The composition of claim 13, wherein the effective amount of the xanthohumol/cyclodextrin complex is 0.001 to 3.0% by weight of the composition.

16. The composition of claim 13, wherein the composition has increased oral availability relative to the xanthohumol alone.

17. A composition comprising a xanthohumol/cyclodextrin complex obtained by combining the xanthohumol and the cyclodextrin in an aqueous mixture and adjusting the pH to 10-12, thereby providing for xanthohumol/cyclodextrin complex formation;
   wherein the xanthohumol is 3'-[3,3-dimethyl allyl]-2',4',4-trihydroxy-6'-methoxychalcone); and
   the cyclodextrin is beta-cyclodextrin.

18. A nutraceutical composition comprising a xanthohumol/cyclodextrin complex in an acceptable carrier;
   wherein the xanthohumol is 3'-[3,3-dimethyl allyl]-2',4',4-trihydroxy-6'-methoxychalcone); and
   the cyclodextrin is beta-cyclodextrin.

19. A non-alcoholic food product comprising a xanthohumol/cyclodextrin complex;
wherein the xanthohumol is 3'-[3,3-dimethyl allyl]-2',4',4-trihydroxy-6'-methoxychalcone); and
the cyclodextrin is beta-cyclodextrin.

20. The food product of claim 19, wherein the food product is selected from the group consisting of milk, tea, soft drink, juice, coffee, seasoning, cereal, water, yogurt, cookies, chewing gum, chocolate, and soup.

21. A dietary supplement comprising a xanthohumol/cyclodextrin complex;
wherein the xanthohumol is 3'-[3,3-dimethyl allyl]-2',4',4-trihydroxy-6'-methoxychalcone); and
the cyclodextrin is beta-cyclodextrin.

22. A pharmaceutical pack comprising a xanthohumol/cyclodextrin complex formulated in individual dosage amounts;
wherein the xanthohumol is 3'-[3,3-dimethyl allyl]-2',4',4-trihydroxy-6'-methoxychalcone); and
the cyclodextrin is beta-cyclodextrin.

23. A method of treating a disease, comprising administering to a subject in need thereof an effective amount of the composition of claim 1, wherein the disease is obesity, type II diabetes, or dyslipidaemia, wherein the disease is mediated by Acyl-CoA diacylglycerol acyltransferase, Acyl-CoA cholesterol acyltransferase, or VEGF.

24. A method of lowering cholesterol levels in a subject in need thereof, comprising administering to the subject an effective amount of the composition of claim 1.

* * * * *